Figure 1:
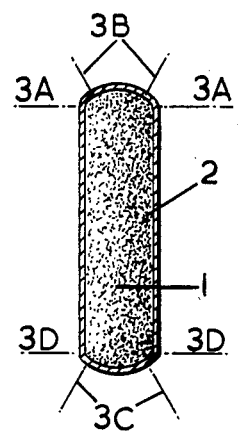

United States Patent [19]

Hemingway et al.

[11] Patent Number: 4,732,764

[45] Date of Patent: Mar. 22, 1988

[54] DEVICE FOR INTRODUCING NUTRIENTS AND/OR THERAPEUTIC MATERIALS INTO RUMINANT ANIMALS

[75] Inventors: Reginald G. Hemingway; Norman S. Ritchie; James J. Parkins, all of Glasgow, Scotland

[73] Assignee: The University Court of the University of Glasgow, Glasgow, Scotland

[21] Appl. No.: 825,687

[22] Filed: Jan. 31, 1986

Related U.S. Application Data

[63] Continuation of Ser. No. 505,191, Jun. 17, 1983, abandoned.

[30] Foreign Application Priority Data

Jun. 22, 1982 [GB] United Kingdom ............... 8218056

[51] Int. Cl.$^4$ ............................................. A23K 1/18
[52] U.S. Cl. .................................................. 424/438
[58] Field of Search ...................... 424/19, 32, 33, 36, 424/438

[56] References Cited

U.S. PATENT DOCUMENTS

| | | | |
|---|---|---|---|
| 3,056,724 | 10/1962 | Marston ............................. | 167/53 |
| 3,507,952 | 4/1970 | Rednick et al. ..................... | 424/22 |
| 3,535,419 | 10/1970 | Siegrist ............................... | 422/22 |
| 3,832,252 | 8/1974 | Higuchi et al. ..................... | 424/19 |
| 3,880,990 | 4/1975 | Bauer et al. ........................ | 424/19 |
| 4,044,119 | 8/1977 | Carlson, Jr. et al. ............... | 424/22 |
| 4,066,754 | 1/1978 | Chou ................................... | 424/229 |
| 4,166,107 | 8/1979 | Miller et al. ........................ | 424/19 |
| 4,196,187 | 1/1980 | Dannelly et al. ................... | 124/19 |

FOREIGN PATENT DOCUMENTS 227098  3/1960  Australia.

OTHER PUBLICATIONS

Blodinger—*Formulation of Veterinary Dosage Forms*, pp. 45–49, 140–143, 172–173, Marcel Dekker, Inc., New York.

*Primary Examiner*—Frederick E. Waddell
*Attorney, Agent, or Firm*—Bell, Seltzer, Park & Gibson

[57] ABSTRACT

The device comprises a core containing nutrient and/or therapeutic material and/or other biologically active material and an insoluble rigid brittle skin enclosing the core. The skin is formed of a synthetic resin, and is arranged to require support of the core to maintain its integrity. The skin may be formed on the core by dipping the core in the liquified resin or by spraying liquified resin on the core.

8 Claims, 7 Drawing Figures

DEVICE FOR INTRODUCING NUTRIENTS AND/OR THERAPEUTIC MATERIALS INTO RUMINANT ANIMALS

CROSS REFERENCE TO RELATED APPLICATION

This application is a continuation of application Ser. No. 505,191 filed June 17, 1983, now abandoned.

The subject of this invention is a device for the easy introduction of nutrients and/or therapeutic materials and/or other biologically active agents into ruminant animals in such a way that the release of the nutrients and/or therapeutic materials is continuous and controlled.

In particular it is concerned with the development of a pellet of such characteristics that it can be swallowed after oral administration and remains to dissolve slowly in the rumeno-reticular sac so that it is neither lost by regurgitation nor by passage in the faeces. The advantage of using such a sustained release device is to avoid the frequent handling or gathering of livestock at regular intervals. Under some extensive grazing situations it may be the only practical means of administration.

Such devices for introducing nutrients, therapeutic materials and other biologically active agents into animals are known. One such customary device is of a cylindrical shape and contains the desired nutrients and/or therapeutic materials. When swallowed by an animal it releases in the animal's rumeno-reticular sac the nutrients and/or therapeutic materials contained therein. It has heretofore been difficult in the use of such devices to ensure that the rate of release of material lies within a chosen range because as the device dissolves away the area exposed to the rumen liquor of the animal usually changes. Certain substances which are essential nutrients or therapeutic materials can cause harm or be ineffective for an extended period if release at too great a rate and of course have little or no effect if released at too low a rate.

Examples of nutrient substances which it is often found desirable to introduce into ruminant animals are vitamins A, D and E and trace elements such as copper and cobalt. Examples of therapeutic substances are parasiticides. Examples of other biologically active agents are growth-promoting substances, immunomodulators and beta adrenergic agonists.

The various known forms of heavy pellet include a cobalt bullet which is a baked ceramic cylinder having a cobalt salt as an ingredient and having an integral density of 4 without the need for any further weighting device. The cobalt leaches out over a period of time into the rumen of the animal but this design of pellets tends to coat over with a deposit of insoluble calcium phosphate and other salts which prevents any further cobalt dissolution. Another example is a magnesium pellet containing metallic magnesium. Small iron shot particles are included to increase the overall pellet density. These are ultimately excreted via the faeces. Whereas it can successfully supply magnesium, its design can only be applied to the supply of elements which can form suitable metal alloys.

Another known form of device consists of active material enclosed within a stainless steel tubular casing closed at the ends by permeable diaphragms. As such a casing is normally about 2.5 cms in diameter and about 10 cms long, the insoluble residue i.e. the steel casing, left by the use of one such device is quite considerable. As the overall specific gravity of the residue is high and above the critical value, the animal cannot expel it. Repeated dosing of the same animal would lead to an increasing number of residual shells retained in the reticulum.

Other known forms or rumen devices include contraptions which extend spring-loaded arms after administration in order to prevent dislodgement of the device from the reticulo-rumen. Such mechanical devices leave considerable metallic and/or plastics residues and incur high manufacturing and retail costs.

These examples illustrate some of the problems associated with the design of a rumen pellet. The two main objectives are to ensure a steady release of the nutrient or therapeutic substance over a chosen length of time and to ensure that the density is sufficiently high to prevent ejection of the pellet. This in most cases entails the inclusion of some heavy material such as iron, preferably in the form which will be excreted or fully metabolised by the animal after it has served its function as a weighting device.

It is an object of the present invention to provide a device which does not suffer from the described disadvantages associated with the known devices.

According to the invention a device for introducing at least one substance of a nutrient and/or therapeutic and/or other biologically active nature into a ruminant animal comprises an elongated pellet incorporating a core the constituents of which include at least one active substance in the form of compressed particles and a rigid skin enclosing the core, said skin being formed of a material which is insoluble in the rumen liquor of the animal and which is sufficiently thin and brittle to require the support of the core to maintain its integrity so that without the support provided by the core it would disintegrate.

The core may also incorporate at least one substance of high specific gravity preferably also in the form of particles.

The device may be rendered capable of supplying doses of the active substance at chosen intervals of time by incorporating strata of unmedicated matrix material in the core at spaced distances along the core such as to provide inactive periods of the device while the unmedicated material is dissolving.

The pellet may be of constant crosssectional area throughout its length or may vary in cross section, for example, it may be coned, so that the rate of release of the active substance may be caused to vary.

The casing may be formed of a coating of a synthetic resin, for example, polyester, epoxy or acrylic resin. Satisfactory skins have been formed by coating the core with a synthetic resin adhesive such as is readily available under several well-known names.

A skin of synthetic resin of thickness 0.1–0.3 mm has been found to be thick enough to be impervious to the rumen liquor of an animal yet weak enough and brittle enough to break off at any portion where the support of the core is removed by dissolution of the core at that position.

The coating may be formed by spraying the core with or dipping the core into a liquid synthetic resin mixed with a hardener before the hardener has operated to cause the resin to solidify. The action of dipping or spraying causes the core to be covered completely so that no separate action requires to be taken to seal the core within the casing.

The material of high specific gravity may be particles or iron or any other metal or salt of a metal of sufficiently high specific gravity to impart to the device a chosen minimum specific gravity usually greater than 2.0, which is about the minimum specific gravity required of any appropriately shaped article which the animal is to retain in its rumen or reticulum. The preferred density is generally in excess of 2.5. The pellet may be made sufficiently rigid for handling purposes by making the particle size of the powders constituting the elements of the pellet of sufficiently small size and compacting them by compressive force. With certain materials cohesion of the particles may be assisted by including a binder preferably of a material harmless to the animal such as starch.

Figure 2:
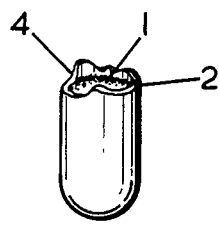
Figure 3:
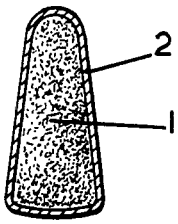

A practical embodiment of the invention is illustrated in the accompanying drawings in which FIG. 1 illustrates in longitudinal section a device in its sealed state, FIG. 2 illustrates a device the core of which has been partly dissolved and FIG. 3 illustrates in longitudinal section a device arranged to provide a rising or falling rate of release of the active substance according to which end is initially opened.

FIGS. 4, 5, 6 and 7 are graphs referred to in the Examples set out at the end of the specification.

In the drawings 1 denotes a core formed of particles of active material and particles of material of a high overall specific gravity and 2 denotes a thin rigid skin of brittle material covering the core. The skin requires the support of the core to maintain its integrity, that is, removal of the support of the core at any point on the skin leaves the skin too weak to resist any force applied to it during the digestive processes in an animal's rumen or stomach. The lines 3A and 3B indicate alternative positions where the device may be sectioned before administration to the animal to expose the other end of the core. Referring to FIG. 2 it will be seen that the skin 2 at the point where the core has dissolved in projecting as an unsupported shell at 4. This thin brittle shell disintegrates almost immediately it is formed in movement of the contents of the rumen during digestion. The tiny shell fragments are harmless to the animal and are expelled in the faeces.

In practice a device is used by cutting the device at 3A or 3B to expose an end face of the core 1. The device may be cut also at 3C or 3D so that both end faces of the core 1 are exposed. The animal is then treated to cause it to swallow the device. The rumen liquor of the animal acting on the exposed end face or faces of the core causes the core to start to dissolve releasing the required material into the rumen or reticulum of the animal. As the core dissolves, the position of the skin 2 formerly covering each dissolved portion of the core is left unsupported and disintegrates. The insoluble particles imparting the high specific gravity of the device are released as the core dissolves and pass through the animal. Since the proportion of the constituent of high specific gravity to the active constituents does not change during the entire active life of the device the overall specific gravity of the device remains substantially constant. Since the skin is a thin coating of light material its contribution to the overall weight of the device is negligible.

The period of sustained release is governed by the chemical composition of the matrix, the length of the pellet and the tabletting pressure used in the forming of the pellet. As the result of the mutual rubbing action a more consistent pattern of degradation may be obtained by the presence of two pellets in the rumeno-reticular sac.

EXAMPLE 1

A mixture was made containing the following materials in the stated percentages:
24.00 levamisole hydrochloride
44.00 copper oxide needles
0.12 cobalt sulphate
0.055 sodium selenite
0.21 potassium iodate
7.72 zinc oxide
1.65 vitamins A and D (500,00:100,000 ius/g)
1.65 vitamin E (500,000 ius/g)
15.26 manganese sulphate
5.33 zinc sulphate.

The component materials were thoroughly mixed, then compressed in a 2.5 cm diameter mould under a pressure of 70 bars in a hydraulic press. The exterior of the resultant bullet-shaped pressing was then hardened slightly by a brief dip in water followed by drying. Three coats of polyester resin were applied with a paint brush each approximately 0.07 mm thick allowing a period of about an hour to elapse between successive coatings. An uncoated surface was left at one end of the bullet for exposure to the rumen environment.

The finished device had a weight of 85 g and a density of 2.8 gcm$^{-3}$. Erosion rate was tested by placing the bullet in the reticulum of a fistulated cow and removing it periodically, weighing and then returning the device to the animal.

Figure 4:
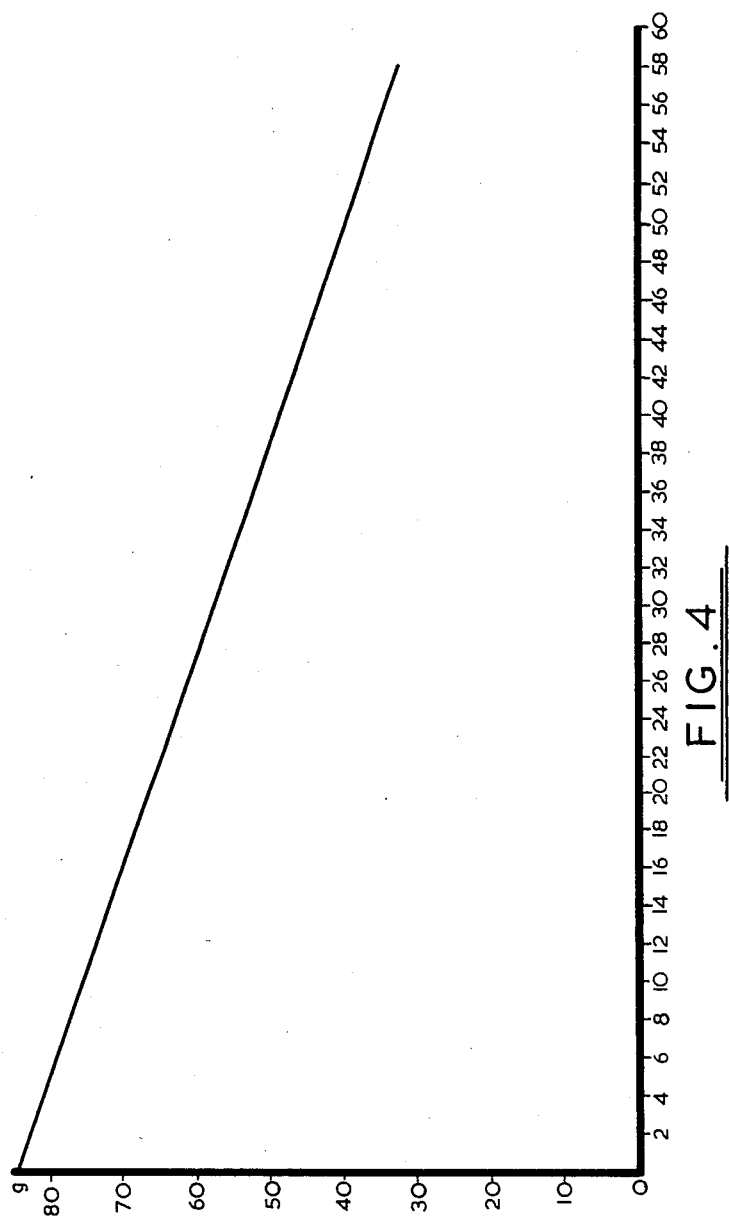

The loss of weight of the core with passage of time is shown in the graph of FIG. 4. It will be noted in this and the other graphs that the rate of loss of weight of the core material is substantially linear. In this and the other graphs the ordinate represents grams and the abscissa represents days.

EXAMPLE 2

The device of this example contains ivermectin in a mineral base. A mixture was made containing the following materials in the stated percentages:
1.79 ivermectin
44.64 copper oxide needles
0.194 cobalt sulphate
0.091 sodium selenite
0.34 potassium iodate
12.93 zinc oxide
2.77 vitamins A and D (500,000:100,000 ius/g)
2.77 vitamin E (500,000 ius/g)
25.55 manganese sulphate
8.93 zinc sulphate The manufacturing method was the same as that employed in Example 1. The ivermectic was thoroughly mixed with the mineral salts and copper oxide needles and then compressed under a pressure of 70 bars in a 1.9 cm diameter mould. After a brief hardening with water, three coats of a commercially obtainable polyester resin were applied, leaving exposed one end surface.

Figure 5:
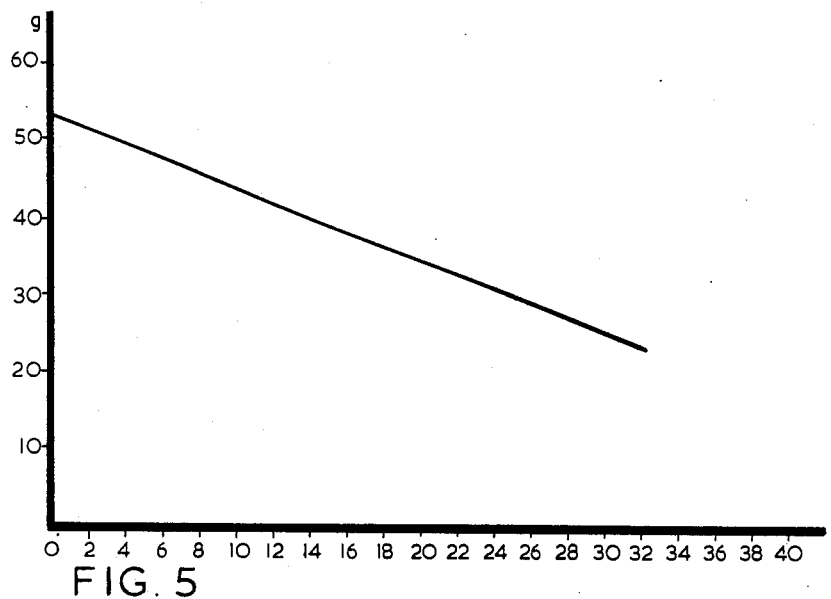

The completed device had a weight of 52 g and a density of 2.87 gcm$^{-3}$. The graph of FIG. 5 shows the change in weight of the device over a period of 32 days in the reticulum of a fistulated cow.

EXAMPLE 3

The device of this example contains the growth promoter monensin sodium. A mixture was made containing the following materials in the stated percentages:
9.06 monensin sodium
46.81 copper oxide needles
3.02 levamisole hydrochloride
0.14 cobalt sulphate
0.064 sodium selenite
0.24 potassium iodate
9.11 zinc oxide
1.95 vitamins A and D (500,000:100,000 ius/g)
1.95 vitamin E (500,000 ius/g)
18.000 manganese sulphate
9.64 zinc sulphate The manufacturing method employed was the same as that of Example 1. The mixture was pressed at a pressure of 70 bars in a 2.5 cm diameter mould. Three layers of a commercially obtainable polyester resin were applied after hardening as described in previous examples. One end surface was left uncoated.

The finished device had a weight of 65 g and a density of 2.8 gcm$^{-3}$. Testing of weight loss was done in a fistulated cow.

Figure 6:
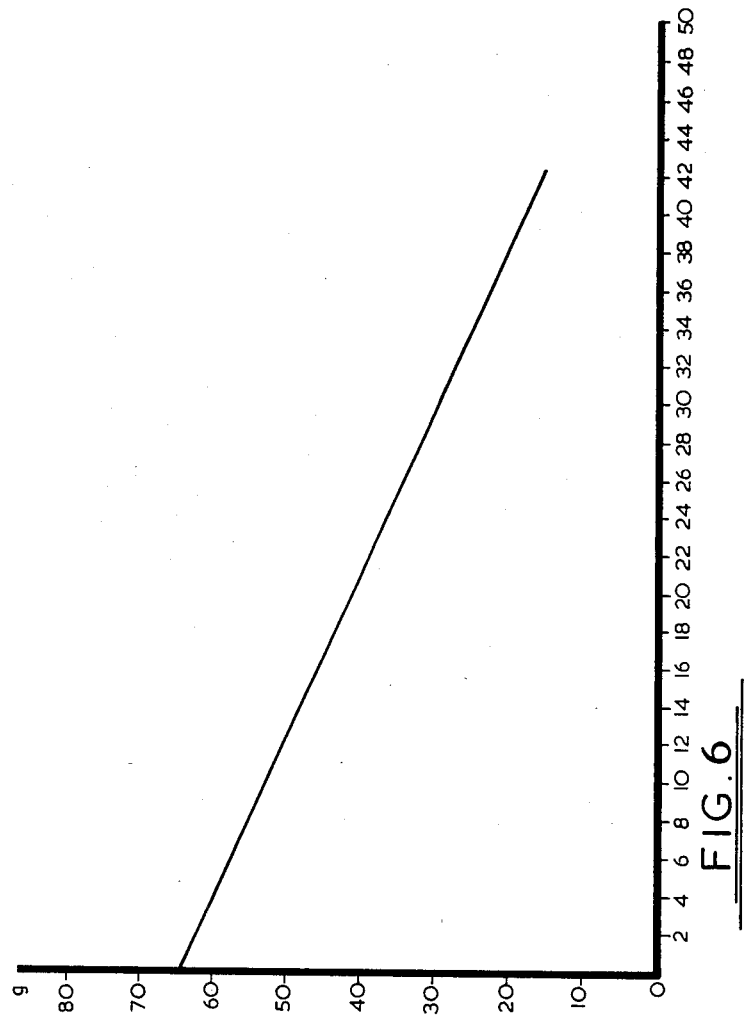

Loss of weight with passage of time is shown in the graph of FIG. 6.

EXAMPLE 4

This is a device intended to supplement minerals and vitamins. A mixture was made containing the following materials in the stated percentages:
45.45 copper oxide needles
0.197 cobalt sulphate
0.093 sodium selenite
0.35 potassium iodate
13.16 zinc oxide
2.82 vitamins A and D (500,000:100,000 ius/g)
2.82 vitamin E (500,000 ius/g)
26.01 manganese sulphate
9.09 zinc sulphate As in the previous examples the mineral salts and copper oxide needles were mixed and pressed at a pressure of 70 bars. A mould of 1.7 cm diameter was used and the density of the pressed mixture was 3.08 gcm$^{-3}$. The same commercially available polyester resin was painted on to provide a coating comprising three layers with a total thickness of about 0.2 mm, with one end of the core left exposed. The total weight of the device was 34 g.

Figure 7:
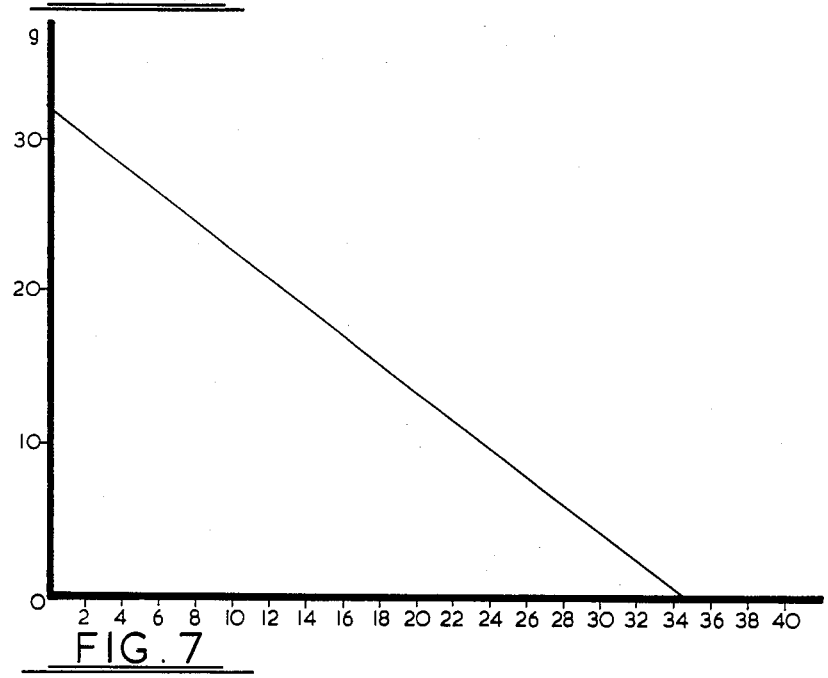

The graph of FIG. 7 shows the gradual dissolution of the core over a period of 33 days in a fistulated cow.

We claim:

1. A pellet for introducing biologically active agents into a ruminant animal, said pellet having a specific gravity of 2.0 or greater so as to be retained in the rumen or reticulum of the ruminant animal and said pellet having a core formed of compressed particles, at least some of which contain a biologically active agent, and a synthetic resin coating forming a rigid skin surrounding said core, said skin being insoluble in the rumen liquor of the animal and having a thinness and brittleness such that the skin requires the support of the core to maintain its integrity, and without the support of the core disintegrates into fragments during the digestive process, and wherein said pellet is sectioned so as to expose said core to the rumen liquor so that the rumen liquor may progressively dissolve the core and release said biologically active agents while the brittle skin is progressively disintegrated as the core is dissolved.

2. A pellet as claimed in claim 1 in which the core includes strata of soluble inactive material at spaced distances along the core.

3. A pellet as claimed in claim 1 in which the pellet is of an elongated configuration and varies in cross section along its length.

4. A pellet as claimed in claim 1 in which the synthetic resin is an acrylic resin.

5. A pellet as claimed in claim 1 in which the synthetic resin is a polyester resin.

6. A pellet as claimed in claim 1 in which the synthetic resin is an epoxy resin.

7. A pellet as claimed in claim 1 in which the core includes particles of a high specific gravity which impart to the pellet a specific gravity in excess of 2.5.

8. A method of administering biologically active agents to ruminant animals, said method comprising
providing a pellet having a specific gravity of 2.0 or greater so that the pellet will be retained in the rumen or reticulum of the ruminant animal, and said pellet having a core formed of compressed particles, at least some of which contain a biologically active agent, and a synthetic resin coating forming a rigid skin surrounding said core and being insoluble in the rumen liquor of the animal and having a thinness and brittleness such that the skin requires the support of the core to maintain its integrity, and without the support of the core disintegrates into fragments during the digestive process,
sectioning the pellet so as to expose the underlying core, and
causing the ruminant animal to swallow the sectioned pellet to thereby deposit the pellet in the rumen of the animal and to thus expose the core to the rumen liquor, whereby the rumen liquor may progressively dissolve the core while the thin brittle skin progressively disintegrates into fragments during the digestive process as the supporting core is dissolved away.

* * * * *